(12) United States Patent
Blackwell et al.

(10) Patent No.: US 7,608,079 B1
(45) Date of Patent: Oct. 27, 2009

(54) UNICONDYLAR KNEE APPARATUS AND SYSTEM

(75) Inventors: Timothy J Blackwell, Warsaw, IN (US); Jacy C Hoeppner, Warsaw, IN (US); Troy W Hershberger, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 895 days.

(21) Appl. No.: 10/794,709

(22) Filed: Mar. 5, 2004

(51) Int. Cl.
*A61F 5/00* (2006.01)
(52) U.S. Cl. .................................... 606/87; 606/86 R
(58) Field of Classification Search ............ 606/79–82, 606/86, 87, 96, 86 R, 176, 179–180, 88–89; 623/20.32–20.34, 20.14
See application file for complete search history.

(56) References Cited

U.S. PATENT DOCUMENTS

| | | | | |
|---|---|---|---|---|
| 1,179,910 A | * | 4/1916 | Greenfield | 606/176 |
| 1,417,669 A | * | 5/1922 | Langworthy | 606/176 |
| 2,260,157 A | * | 10/1941 | Zwick | 409/89 |
| 4,409,973 A | * | 10/1983 | Neufeld | 606/82 |
| 4,952,213 A | | 8/1990 | Bowman et al. | |
| 5,047,032 A | | 9/1991 | Jellicoe | |
| 5,053,039 A | * | 10/1991 | Hofmann et al. | 606/87 |
| 5,171,244 A | | 12/1992 | Caspari et al. | |
| 5,228,459 A | | 7/1993 | Caspari et al. | |
| 5,263,498 A | | 11/1993 | Caspari et al. | |
| 5,304,181 A | * | 4/1994 | Caspari et al. | 606/80 |
| 5,312,411 A | | 5/1994 | Steele et al. | |
| 5,409,489 A | | 4/1995 | Sioufi | |
| 5,468,243 A | | 11/1995 | Halpern | |
| 5,486,180 A | | 1/1996 | Dietz et al. | |
| 5,534,005 A | * | 7/1996 | Tokish et al. | 606/80 |
| 5,556,399 A | | 9/1996 | Huebner | |
| 5,569,285 A | * | 10/1996 | Webb | 606/180 |
| 5,616,146 A | | 4/1997 | Murray | |
| 5,643,272 A | | 7/1997 | Haines et al. | |
| 5,676,668 A | | 10/1997 | McCue et al. | |
| 5,681,316 A | | 10/1997 | DeOrio et al. | |
| 5,690,636 A | | 11/1997 | Wildgoose et al. | |
| 5,788,701 A | | 8/1998 | McCue | |
| 5,908,424 A | * | 6/1999 | Bertin et al. | 606/88 |
| 5,976,145 A | | 11/1999 | Kennefick, III | |
| 6,063,091 A | | 5/2000 | Lombardo et al. | |
| 6,228,091 B1 | | 5/2001 | Lombardo et al. | |
| 6,355,045 B1 | * | 3/2002 | Gundlapalli et al. | 606/88 |
| 6,482,209 B1 | | 11/2002 | Engh et al. | |
| 6,551,324 B2 | | 4/2003 | Müller | |
| 2004/0102785 A1 | | 5/2004 | Hodorek et al. | |
| 2005/0021038 A1 | * | 1/2005 | Maroney | 606/87 |
| 2005/0192588 A1 | * | 9/2005 | Garcia | 606/88 |

* cited by examiner

*Primary Examiner*—Thomas C Barrett
*Assistant Examiner*—James L Swiger
(74) *Attorney, Agent, or Firm*—Harness, Dickey

(57) ABSTRACT

A device for resecting a bone to receive an implant comprising a resection guide and a cutting device. The resection guide is operable to be secured to a bone. The cutting device operable to cut the bone. The cutting device is received by the resection guide and directed to the bone by the resection guide. The resection guide restricts movement of the cutting device to form a resected portion within the bone, the resected portion at least substantially surrounded by a bone rim.

28 Claims, 9 Drawing Sheets

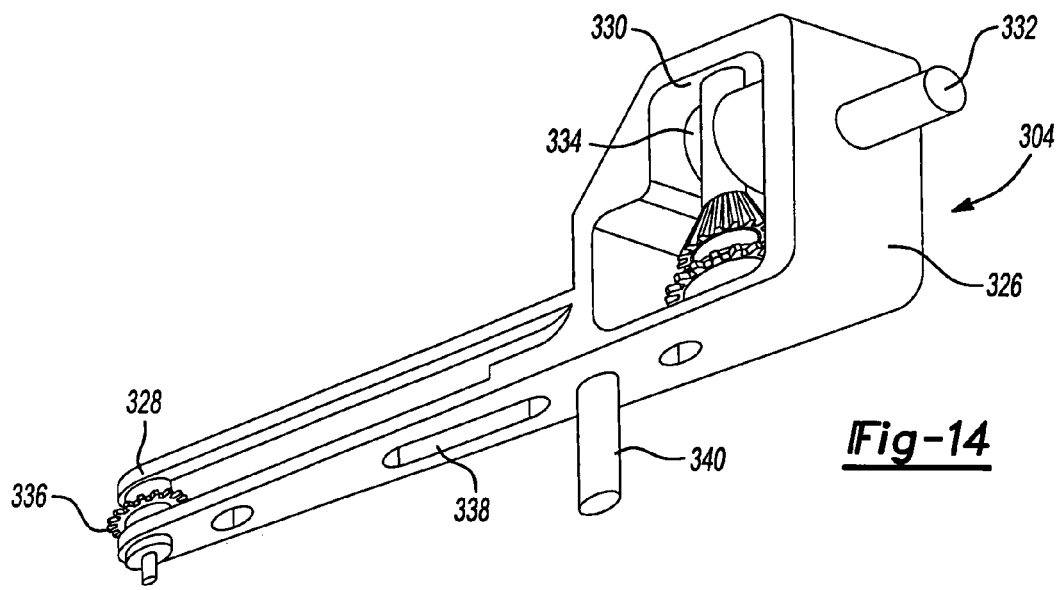
*Fig-14*
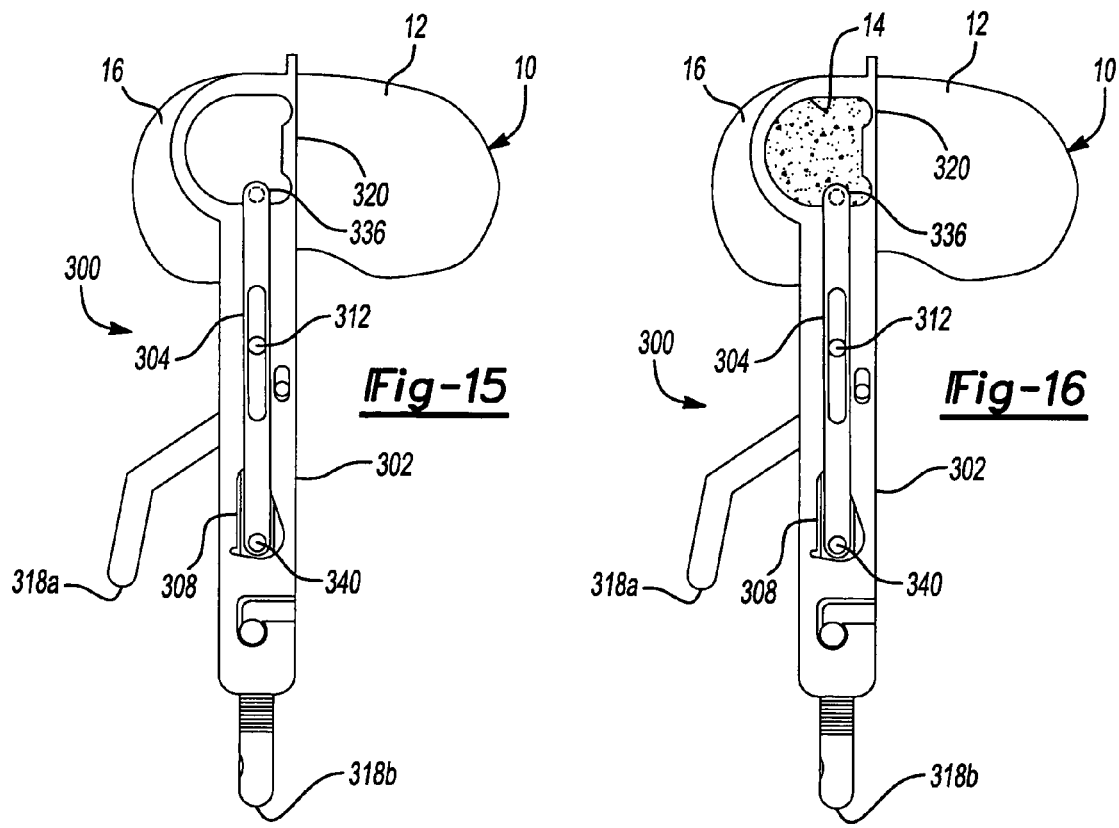
*Fig-15*  *Fig-16*

UNICONDYLAR KNEE APPARATUS AND SYSTEM

FIELD OF THE INVENTION

The present invention relates to a method and apparatus for preparing bone to receive an implant. In particular, the present invention relates to a method and apparatus for preparing a knee joint to receive a unicondylar knee system.

BACKGROUND OF THE INVENTION

It is not uncommon for patients to experience damaged or defective bones. Bone damage at the knee joint, such as damage caused by osteoarthritis, is particularly common. Osteoarthritis is a disease of the cartilage present at the knee joint. Osteoarthritis is a degenerative process in which cartilage present between the tibia and femur erodes. As this cartilage erodes, contact between the tibia and femur bones occurs, causing damage to the tibia and femur.

When only one side of the knee is affected, the damaged portions of the tibia and/or femur are removed and each are replaced with implants, conventionally referred to as a unicompartmental knee replacement. With respect to the tibia, the superior articulating surface of the tibia bone is conventionally prepared to receive the implant by resecting a substantial portion of the superior articulating bone surface, including all of, or a substantial portion of, the bone rim at the periphery of the articulating surface. However, it is desirable to preserve as much of the peripheral rim of the articulating surface as possible for a variety of reasons, such as to better secure the implant to the tibia and to maintain the structural integrity of the tibia. With respect to the femur, the inferior articulating surface is conventionally prepared by resecting a substantial portion of the inferior articulating surface. However, it is desirable to preserve as much of the natural femur as possible to, for example, maintain the structural integrity of the bone. Thus, there is a need for an apparatus and/or method for resecting the superior articulating surface of the tibia and the inferior articulating surface of the femur to preserve as much of the natural bone surfaces as possible.

SUMMARY OF THE INVENTION

The present invention provides for a device for resecting a bone to receive an implant comprising a resection guide and a cutting device. The resection guide is operable to be secured to a bone. The cutting device is operable to cut the bone. The cutting device is received by the resection guide and directed to the bone by the resection guide. The resection guide restricts movement of the cutting device to form a resected portion within the bone, the resected portion at least substantially surrounded by a bone rim.

The present invention further provides for a device for forming a resected portion at a superior surface of a tibia bone to receive an implant comprising a resection guide and a cutting device. The resection guide is operable to be secured to the bone having a guide block that includes a guide track. The cutting device is operable to cut the bone and form the resected portion comprising at least one mating device operable to cooperate with the guide track. Cooperation between the guide track and the mating device restricts movement of the cutting device to a region of the superior surface having the resected portion, the resected portion at least substantially surrounded by a bone rim.

Still further, the present invention provides for a device for forming a resected portion at a superior surface of a tibia bone to receive an implant. The implant comprises a resection guide operable to be secured to the bone and a cutting device having a cutting portion operable to be guided to the superior surface of the bone by the resection guide. The cutting portion has dimensions substantially similar to the resected portion. The cutting portion, guided by the resection guide, is driven within the bone to form the resected portion, the resected portion being at least substantially surrounded by a bone rim.

The present invention also provides for a device for forming a resected portion at a superior surface of a tibia bone to receive an implant comprising a resection guide, a cutting device, and a positioning jig. The resection guide is secured to the bone and has a receptor with dimensions substantially similar to dimensions of the resected portion. The cutting device is operable to cut the bone. The positioning jig is in cooperation with the receptor and is operable to maneuver the cutting device. The positioning jig confines contact between the cutting device and the bone to the superior surface and cooperation between the positioning jig and the receptor prevents the cutting device from resecting the superior surface beyond the resected portion.

The present invention also provides for a method for forming a resected portion within a superior surface of a tibia bone to receive an implant that includes the steps of securing a resection guide to the bone and cutting the bone to form the resected portion and a bone rim at least substantially surrounding the resected portion using a cutting device guided by the resection guide. Cooperation between the resection guide and the cutting device restricts movement of the cutting device to an area defined by the resected portion.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 14 is a perspective view of a milling device of the fourth bone preparation device of FIG. 12;

FIG. 15 is a top view illustrating the use of the fourth bone preparation device of FIG. 12 to prepare a bone to receive an implant;

FIG. 16 is a top view illustrating a bone that has been prepared to receive an implant using the fourth bone preparation device illustrated in FIG. 12;

DETAILED DESCRIPTION OF THE PREFERRED EMBODIMENTS

The following description of the embodiments is merely exemplary in nature and is in no way intended to limit the invention, its application, or uses.

Figure 1:
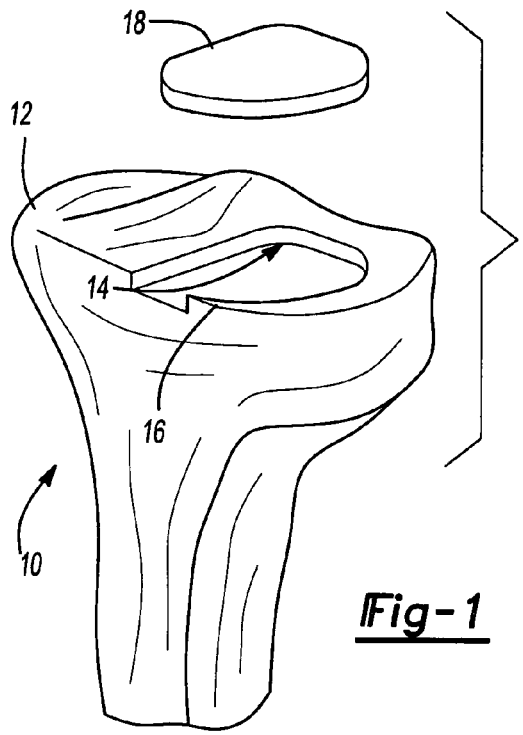
FIG. 1 is a perspective view of a superior portion of a tibia bone, a superior articulating surface of the bone prepared to receive an implant using a method and device of the present invention.
Figure 2:
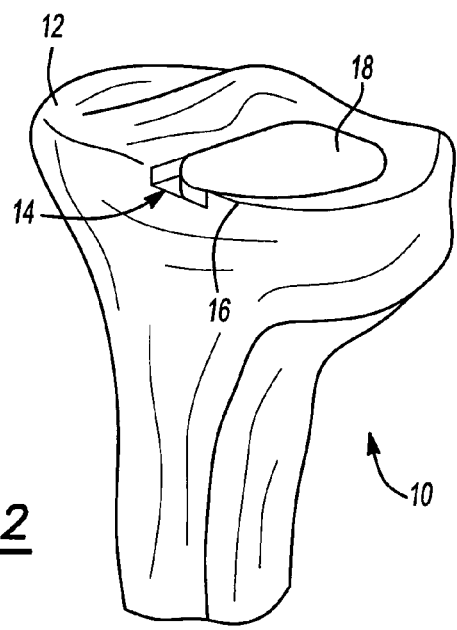
FIG. 2 is a perspective view of the bone of FIG. 1 with the implant seated within the articulating surface of the bone.

With reference to FIG. 1 and FIG. 2, a superior portion of a tibia bone prepared using a method and apparatus of the present invention is illustrated at 10. While certain apparatuses and methods of the present invention are described and illustrated in conjunction with the tibial bone 10, this is for exemplary purposes only as the present invention may be used to prepare a variety of different bones to receive one or more implants. Further, while the bone preparation is often described as a resection process, it must be understood that resection can include any type of cutting, drilling, milling and bone removal.

The prepared tibia 10 generally includes a superior articulating surface 12 having a resected portion 14. The resected portion 14 is at least substantially surrounded by a peripheral tibial rim 16. As illustrated in FIG. 1 and FIG. 2, the tibial rim 16 does not completely surround the resected portion 14. However, as more completely described below, the method and apparatus of the present invention is operable to form the resected portion 14 in which the rim 16 does completely surround the resected portion 14. Seated within the resected portion 14 is an implant 18. The resected portion 14 and the implant 18 may be of any suitable shape but are typically complementary shapes to provide a secure fit between the implant 18 and the resected portion 14. For example, both the resected portion 14 and the implant 18 may have complementary "D" shapes, as illustrated.

Figure 3:
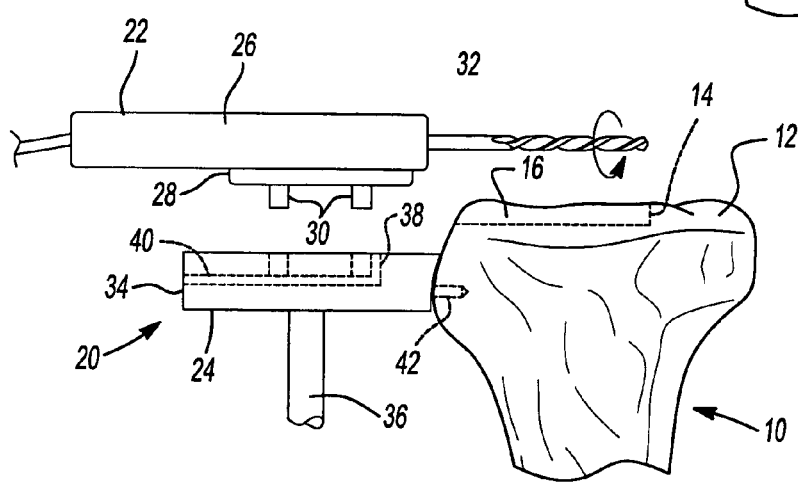
FIG. 3 is a side view of a bone preparation device according to an embodiment of the present invention, the preparation device operable to prepare the superior articulating surface of a tibia to receive an implant.
Figure 4:
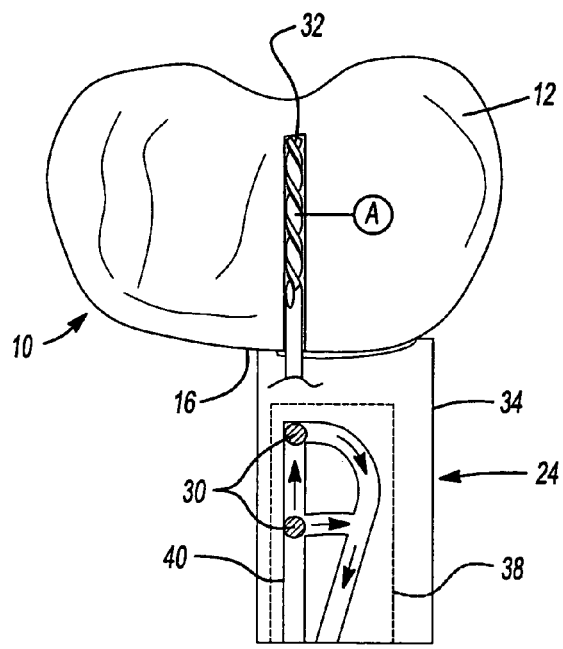
FIG. 4 is a top view of the bone preparation device of FIG. 3, the device located at a first position.
Figure 5:
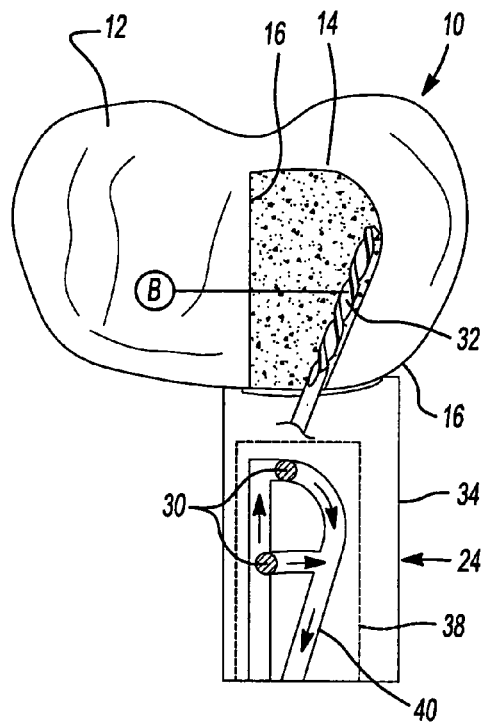
FIG. 5 is a top view of the bone preparation device of FIG. 3, the device located at a second position.

With additional reference to FIGS. 3 through 5, formation of the resected portion 14 according to an embodiment of the present invention using a first bone preparation device 20 is illustrated. The first device 20 generally includes a cutting device, such as a mill 22, and a guide 24. The mill 22 is generally comprised of a body 26 and a base 28. The base 28 and/or the body 26 may be provided with a height adjustment mechanism (not shown) to vary the height of the body 26 above the base 28. Extending from the base 28 is at least one mating device, such as a guide cam or pin 30. While the guide pins 30 are illustrated as cylindrical protrusions, the guide pins 30 may be of any suitable shape, such as square, and may be any suitable mating device operable to mate the mill 22 with the guide 24. Also extending from the body 26 is a cutting device, such as cutting burr 32. The cutting burr 32 is rotated by the body 26 at high speed and is operable to form the resected portion 14 in the tibia.

The guide 24 generally includes a guide block 34 and a guide frame 36. As best illustrated in FIGS. 4 and 5, the guide block 34 includes an insert 38 having a guide track 40. The guide track 40 is typically recessed within the insert 38, however, the guide track 40 may extend from the insert 38 or may be of any suitable configuration to cooperate with the guide pin 30. The guide track 40 is shaped such that movement of the guide pins 30 within the guide track 40 restricts movement of the cutting burr 32 in the direction(s) required to form the resected portion 14. The configuration of the guide track 40 may be altered to form resected portions 14 of different sizes and shapes in addition to the illustrated "D" shape. Different inserts 38 having guide tracks 40 of various shapes may be used with the guide block 34 to form resected portion 14 of the proper size and shape required for the patient as determined by the operating surgeon. The guide block 34 further includes at least one stabilization device, such as a pin 42, for securing the guide block 34 to the superior portion of the tibia 10.

As illustrated in FIG. 3, the guide frame 36 extends from the guide block 34. The guide frame 36 typically extends approximately the entire length of the tibia. At the inferior end of the guide frame 36, which is opposite the guide block 34, is a stabilization device (not shown) for securing the guide 24 to the tibia 10. The stabilization device typically secures to the ankle region.

The operation of the first bone preparation device 20 will now be described in detail. The guide 24 is first secured to the tibia 10. In particular, the guide block 34 is typically positioned at the superior portion of the tibia 10 at or near the superior articulating surface 12 and is secured to the superior portion of the tibia 10 using the stabilization pin 42. The stabilization device (not shown), located at the end of the guide frame 36 opposite the guide block 34, is secured to an inferior portion of the tibia 10, typically near the ankle. The depth of the resected portion 14 depends upon, in part, the superior/inferior positioning of the guide 24 on the tibia 10. For example, the depth of the resected portion 14 increases as the guide 24 is moved to a more inferior position on the tibia 10. Further, the depth of the resected portion 14 depends upon, in part, the height of the body 26 above the base 28 as set by the height adjustment mechanism (not shown) of the mill 22. If the body 26 is extended far above the base 28 then the mill 22 will only make a shallow cut within the superior articulating surface 12 and a shallow resected portion 14. If the body 26 is not extended from the base 28 then the resected portion 14 will be deeper.

The guide 24 is secured in position and the proper guide track 40 is selected by the physician according to the desired size and shape of the resected portion 14. The insert 38 having the desired guide track 40 is next placed in the guide block 34 and the mill 22 is activated and placed upon the guide block 34 such that the guide pins 30 cooperate with the guide track 40. When the guide track 40 has a configuration resembling a "D", as illustrated in FIGS. 4 and 5, the mill 22 is maneuvered in the posterior direction, toward the tibia 10, so that the cutting burr 32 is at position A (FIG. 4) where it engages the superior articulating surface 12 and resects the surface 12 and the rim 16 to form part of the resected portion 14. The cutting burr 32 is guided to position A by interaction between the guide pins 30 and the guide track 40.

With reference to FIG. 5, the mill 22 and associated cutting burr 32 are next moved from position A to position B to form the remainder of the resected portion 14. Movement from position A to position B also resects an additional portion of the rim 16. Movement of the cutting burr 32 from position A to position B is guided by the interaction between the guide pins 30 and the guide track 40. Specifically, the shape of the guide track 40 and the interaction between the guide pins 30 and the guide track 40 restricts movement of the cutting burr 32 to position A, position B, and points in between. If it is desirable to move the drill burr 32 to another position other than position A, position B, or points in between, a different insert 38 having a guide track 40 of a different size and shape may be used. After the resected portion 14 is formed, the first preparation device 20 is removed from the tibia 10 and the implant 18 is implanted within the resected portion 14. The implant 18 may optionally be secured in position using a suitable adhesive, such as bone cement.

With reference to FIGS. 6 through 9, a second preparation device 100 for forming the resected portion 14 within the superior articulating surface 12 of the tibia 10 will now be described in detail. The second device 100 is generally comprised of a guide 102, a positioning jig 104, a cutting device, such as a drill 106, and an alignment template 108.

The guide 102 includes a first end 110 and a second end 112. The first end 110 has a receptor for receiving the positioning jig 104. The receptor typically takes the form of a recessed portion 114 that is recessed within the guide 102. However, the receptor may be of any suitable configuration to receive the jig 104. The recessed portion 114 has a shape that is similar to the desired shape of the resected portion 14 and acts as a guide for cutting the resected portion 14 within the tibia 10. The second end 112 of the guide 102 is secured to the superior tibia 10 by a suitable device, such as a positioning pin 116. Optionally, the guide 102 may also be secured to the inferior tibia using an inferior support (not shown).

The positioning jig 104 is seated within the recessed portion 114. The positioning jig 104 is movable within the recessed portion 114 and adjustable in a wide variety of dimensions. For example, to vary the height of the jig 104 the jig 104 includes a telescoping member 117 that may be locked at a particular height by actuating a thumb screw 119 to tighten a sleeve 121 around the telescoping member 117. To vary the height of the jig 104, and thus the height or depth of the drill 106 at the bone 10, any other suitable type of height variation device or system may be used, such as a rack and pinion system, which is commonly known in the art. Adjusting the height of jig 104 allows the operator to vary the depth of the resected portion 14 without having to remove and reset the guide 102. The positioning jig 104 may comprise the cutting device and/or the drill 106.

The drill 106 is supported by the positioning jig 104. The drill 106 may be any suitable device capable of cutting bone. Typically, the drill 106 is comprised of a drill bit 118 suspended at the end of an elongated support arm 120. The elongated support arm 120 is adjustably secured to the positioning jig 104 to permit adjustment of the drill 106 in a variety of different dimensions to insure optimal positioning of the drill 106 in relation to the superior articulating surface 12. For example, the drill 106 may be adjusted in a horizontal and vertical dimension in relation to the superior articulating surface 12 of the tibia 10.

To maintain contact between the drill bit 118 and the superior surface 12, the jig 104 is spring-loaded to exert a downward force upon the drill 106 in the direction of the superior surface 12.

Figure 6:
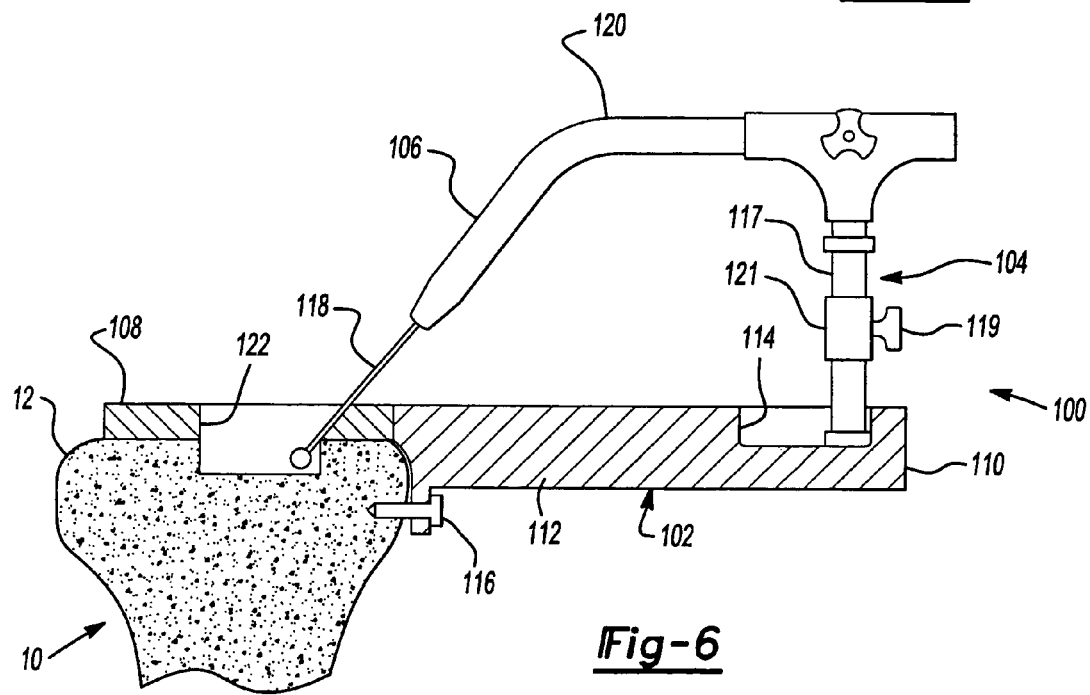
FIG. 6 is a side view of a bone preparation device according an additional embodiment of the present invention, the bone preparation device including an alignment template and operable to prepare the superior articulating surface of a tibia to receive an implant.
Figure 7:
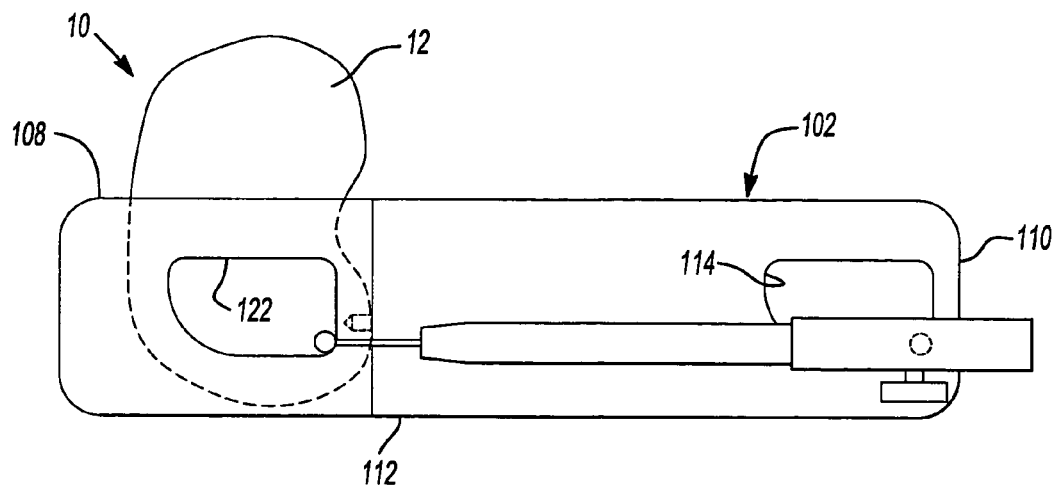
FIG. 7 is a top view of the bone preparation device of FIG. 6.

Alignment template 108 is used to properly calibrate or "zero" the drill 106 at the superior surface 12. As seen in FIGS. 6 and 7, the alignment template 108 includes an outline 122 of the resected portion 14. The alignment template 108 is positioned on the articulating surface 12 and is secured to the articulating surface 12, and optionally the guide 102, in any suitable manner. The dimensions of the outline 122 are substantially similar to the dimensions of the resected portion 14 and the dimensions of the recessed portion 114 of the guide 102. To provide a resected portion 14 having dimensions different than illustrated, a guide 102 having a recessed portion 114 of a different size and shape than that shown may be used.

With continuing reference to FIGS. 6 and 7, and additional reference to FIGS. 8 and 9, preparation of the resected portion 14 using the second bone preparation device 100 is illustrated and will now be described. The guide 102 of the second preparation device 100 is secured to a superior region of the tibia 10 using the positioning pin 116, or any suitable fastening device or method. Optionally, the guide 102 may be further anchored to the tibia 10 by an inferior support (not shown) that engages an inferior region of the tibia 10. Further, the alignment template 108 is seated upon the superior articulating surface 12 and is optionally secured to the guide 102. The alignment template 108 is positioned such that the outline 122 of the guide 102 is at the region of the superior articulating surface 12 where the resected portion 14 is desired.

With the guide 102 secured to the tibia 10 and the template 108 positioned upon the superior articulating surface 12, the positioning jig 104 is calibrated or "zeroed" so that the position of the jig 104 within the recessed portion 114 is substantially equivalent to the position of the drill bit 118 within the outline 122. For example, as illustrated in FIG. 7, the positioning jig 104 is moved to a corner of the recessed portion 114 and the position of the drill 106 is adjusted so that it is positioned in the same corner of the outline 122. After this calibration process is complete, the alignment template 108 is removed from the superior surface 12. Because the dimensions of the recessed portion 114 are substantially similar to the dimensions of the outline 122, movement of the positioning jig 104 within the recessed portion 114 restricts movement of the drill bit 118 to within the area defined by the outline 122, even after the outline 122 is removed from the superior surface 12.

Figure 8:
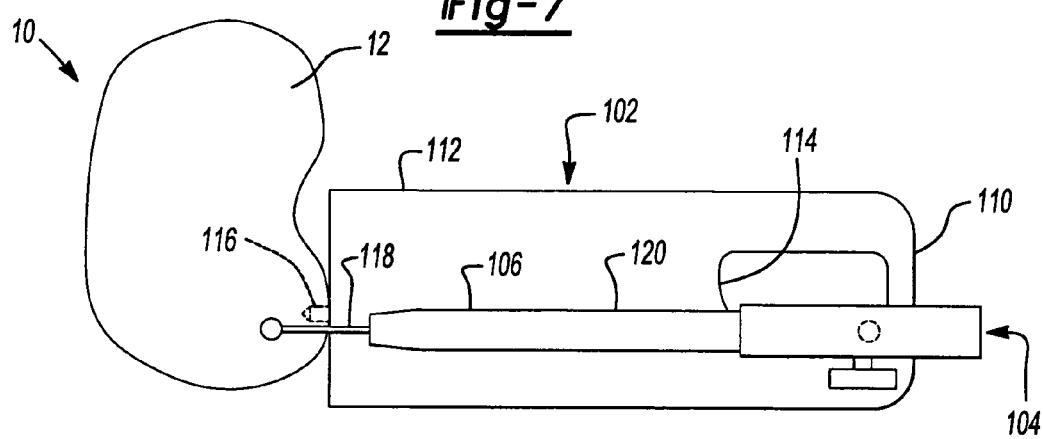
FIG. 8 is a top view of the bone preparation device of FIG. 6 with the alignment template removed.
Figure 9:
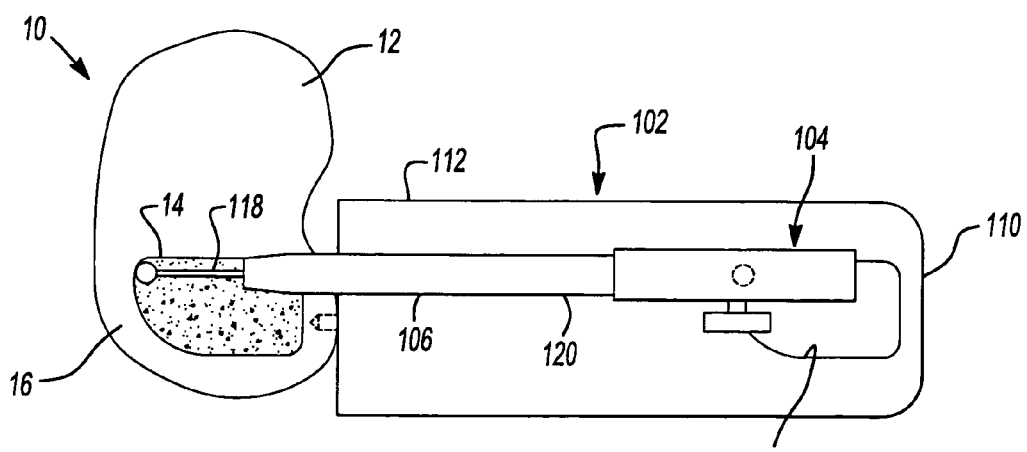
FIG. 9 is a top view of the bone preparation device of FIG. 6 and a superior articulating surface of a tibia that has been prepared using the bone preparation device.

With reference to FIGS. 8 and 9, after the positioning jig 104 and the drill 106 are zeroed, the drill 106 is activated. To form the resected portion 14, the positioning jig 104 is moved within the recessed portion 114 so that it follows or traces the periphery of the resected portion 114. Because the recessed portion 114 has substantially the same dimensions as the outline 122 and the desired resected portion 14, movement of the resection jig 104 about the recessed portion 114 cuts out the resected portion 14 in the superior surface 12. Movement of the positioning jig 104 is confined to movement within the recessed portion 114, thus preventing the drill bit 118 from cutting the superior articulating surface 12 at points beyond of the resected portion 14. If it is desired that the resected portion 14 be of a different size and shape than illustrated, the guide 102 may be replaced with a different guide 102 having recessed portion 114 of a different shape and size to produce a resected portion 14 having the desired shape and size.

As illustrated in FIG. 9, use of the second preparation device 100 to form the resected portion 14 retains the entire rim 16 about the resected portion 14. Because the drill bit 118 is mounted at the end of the elongated support arm 120, which is supported above the superior surface 12 by the positioning jig 104, no portion of the rim 16 is removed during formation of the resected portion 14. After the resected portion 14 is formed, the guide 102 is removed from the tibia 10 and the implant 18 is seated and secured within the resected portion 14.

Figure 10:
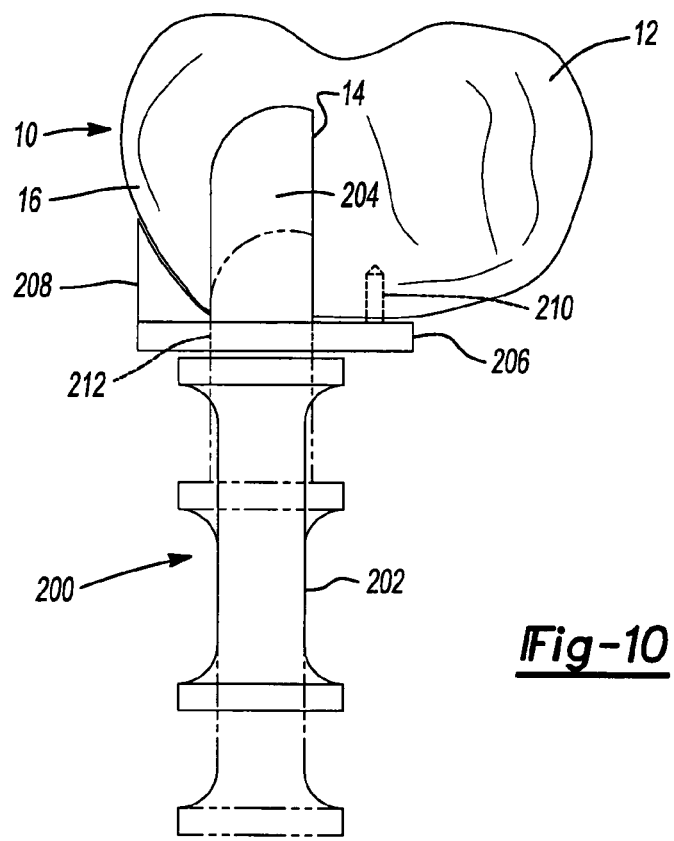
FIG. 10 is top view of a bone preparation device according to an additional embodiment of the present invention, the device engaging a superior articulating surface of a tibial bone.
Figure 11:
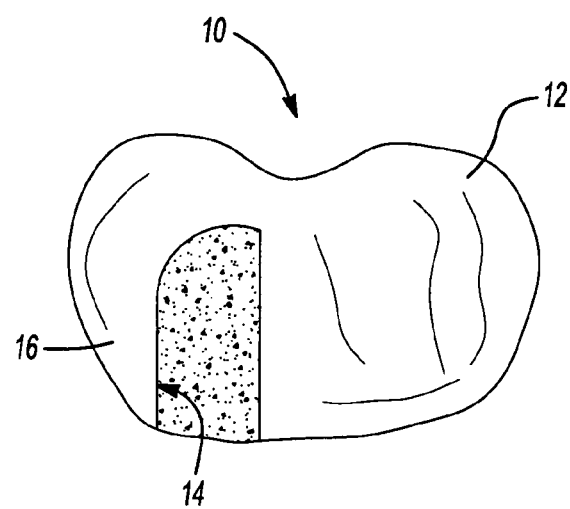
FIG. 11 is a top view of the tibial bone prepared using the bone preparation device of FIG. 10.
Figure 12:
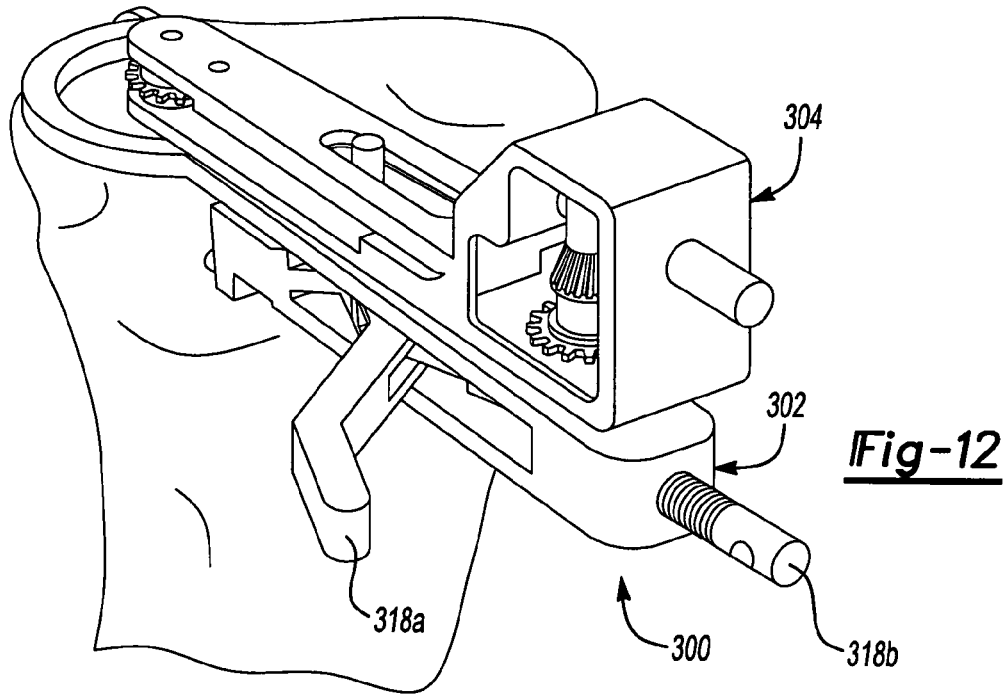
FIG. 12 is a perspective view of a fourth bone preparation device according to an embodiment of the present invention.

With reference to FIGS. 10 and 11, preparation of the resected portion 14 using a third bone preparation device 200 is illustrated. The third preparation device 200 generally includes a handle 202, a cutting portion 204, and a guide 206. The handle 202 and the cutting portion 204 are preferably of a single unit so that manipulation of the cutting portion 204 may be effectuated by maneuvering the handle 202. The handle 202 may be any suitable device capable of being grasped and/or maneuvered, either directly or indirectly by way of, for example, a robotic or computerized device, a surgeon, or other personnel.

The cutting portion 204 may be any device capable of cutting bone to form the resected portion 14. Typically, the cutting portion 204 includes a sharpened knife edge. The cutting portion 204 is typically shaped similar to the desired shape of the resected portion 14.

The guide 206 includes a locating feature 208, a fastening device 210, and a device, typically in the form of a through hole 212, for receiving the cutting portion 204 and/or the handle 202. The locating feature 208 is any suitable device that typically extends from the guide 206 to contact the tibia 10 to assist in aligning the guide 206 in proper position at or near the superior articulating surface 12 of the tibia 10. As illustrated in FIGS. 9 and 10, the locating feature 208 may be curved to correspond to the surface of the tibia 10. The fastening device 210 is typically a screw or pin that engages the tibia 10 to secure the guide 206 to the tibia 10. The through hole 212 is sized to receive the cutting portion 204 and directs the cutting portion 204 to engage the superior surface 12 of the tibia 10.

With reference to FIGS. 10 and 11, use of the third preparation device 200 will now be described. The guide 206 is first mounted to the tibia 10, typically at or near the superior surface 12 of the anterior side of the tibia 10, and the through hole 212 is aligned at the point where the resected portion 14 is desired. The guide 206 is typically mounted to the tibia 10 using the fastening device 210. After the guide 206 is mounted in position, the cutting portion 204 is driven through the hole 212 and into the tibia 10 at a point inferior to the superior surface 12. The cutting portion 204 is then raised toward the superior surface 12 to extract a portion of surface 12 and to form the resected portion 14 so that the rim 16 still substantially surrounds the resected portion 14. As seen in FIG. 11, driving the cutting portion 204 into the side of the tibia 10 removes a portion of the rim 16 surrounding the resected portion 14. After the resected portion 14 is formed, the cutting portion 204 and the guide 206 are removed from the tibia 10 and the implant 18 is seated and secured within the resected portion 14.

With reference to FIGS. 12 through 16, preparation of the resected portion 14 using a fourth bone preparation device 300 is illustrated. The fourth device 300 is generally comprised of a guide 302 and a cutting device 304 mounted upon the guide 302.

Figure 13:
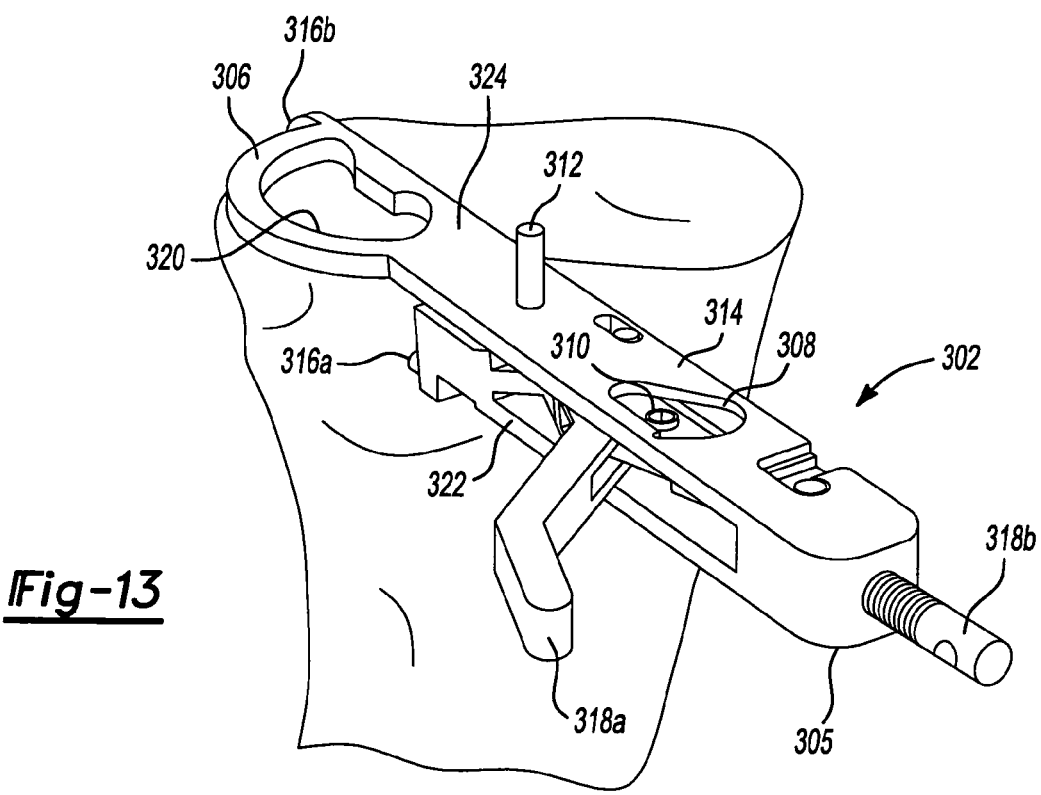
FIG. 13 is a perspective view of a guide of the fourth bone preparation device of FIG. 12.

With particular reference to FIG. 13, the guide 302 generally includes a first end 305 and a second end 306. At or near the first end 305 is a guide track 308 for receiving the cutting device 304. The guide track 308 typically takes the form of a recessed portion that is recessed within the guide 302. However, the guide track 308 may be of any suitable configuration to receive the cutting device 304. The guide track 308 has a shape that is similar to the desired shape of the resected portion 14 and acts as a guide for cutting the resected portion 14 within the tibia 10. The guide track 308 may include a suitable receptor 310 for receiving the cutting device 304 and retaining the cutting device 304 within the guide track 308.

The guide may further include a support device 312 often positioned between the first end 305 and the second end 306. The support device 312 typically takes the form of a post that extends from an upper surface 314 of the guide 302. The support device 312 cooperates with the cutting device 304 to maintain a desired orientation between the guide 302 and the cutting device 304. The guide 302 also includes anchoring devices operable to secure the guide 302 to the tibia 10. The anchoring devices typically take the form of pins 316a and 316b located at the second end 306. Pins 316a engage a first vertical surface of the tibia 10 and pins 316b engage a second vertical surface of the tibia 10, the first surface typically being opposite the second surface. The distance between the pins 316a and 316b can be varied through actuation of handles 318a and 318b, typically located at first end 305.

Second end 306 further includes an outline or template 320 that defines the portion of the tibia 10 to be milled using cutting device 304. The template 320 surrounds the rim portion of the superior surface 12 where the resected portion 14 is to be formed and thus typically includes dimensions that are closely similar to the dimensions of the resected portion 14. The template 320 restricts movement of the cutting device 304 such that the cutting device 304 forms resected portion 14 and does not cut any other portion of the superior articulating surface 12.

The guide 302 comprises a base 322 and a template insert 324. The base 322 includes receptor 310, handles 318a and 318b, and pins 316a. The insert 324 includes guide track 308, support device 312, template 320, and pins 316b. The insert 324 may be secured to base 322 typically using one or more suitable fastening devices that securely fasten the base 322 to the insert 324 but permit the removal of the insert 324 from the base 322 and the replacement of insert 324 with a different insert 324 outfitted with a guide track and a template having dimensions that are different than those of guide track 308 and template 320. The use of an interchangeable insert 324 with base 322 makes the guide 302 operable to form resected portion 14 of various different shapes and sizes to customize the dimensions of resected portion 14 and implant 18 to the needs of the patient.

With particular reference to FIG. 14, the cutting device 304 generally includes a first end 326 and a second end 328. The first end 326 has a drive mechanism 330. The drive mechanism 330 includes an external coupling device, typically in the form of a drive rod 332. The drive rod 332 is engaged by and receives power from an external power supply or drill (not shown). The drive rod 332 transfers power to interior components of the drive mechanism 330, which may include gears 334. The gears 334 transfer power to drill head 336 positioned at second end 328. The drill 336 may be any suitable device capable of milling or resecting the superior articulating surface 12 of the tibia 10.

Typically located between the first end 326 and the second end 328 may be one or more guide devices, usually taking the form of one or more recesses 338. The recesses 338 are configured to cooperate with corresponding support devices 312 of the guide 302. This cooperation helps to maintain the proper relationship between the guide 302 and the cutting device 304. The cooperation between support device 312 and the recess 338 is flexible to permit horizontal movement of the cutting device 304, with respect to the guide 302, in a sliding and rotating manner.

The cutting device 304 may further include a directional device, typically in the form of a directional post 340. The post 340 may be typically located near first end 326. The post 340 is operable to cooperate with the receptor 310 of the guide 302.

With additional reference to FIGS. 15 through 16, preparation of the resected portion 14 using the fourth bone preparation device 300 is illustrated and will now be described. The guide 302 of the fourth preparation device 300 is positioned at the superior region of the tibia 10 such that the template 320 is aligned at the portion of the superior articulating surface 12 where the resected portion 14 is desired. The guide 302 is secured to the tibia 10 by pins 316, which engage the tibia 10. Typically, the pins 316 may be formed to only slightly penetrate the tibia 10, if at all, to maintain the integrity of the tibia 10 and prevent the tibia 10 from being damaged. Engagement of the tibia 10 is effectuated by decreasing the distance between pins 316a and 316b after the template 320 and the pins 316 are in proper position at the superior surface 12 of the tibia 10, such that the pins 316a and 316b act as a vice grip on the tibia 10. The distance between the pins 316 is altered through actuation of the handles 318.

After the guide 302 is in proper position, the cutting device 304 is coupled to the guide through interaction between the support device 312 and recess 338, as well as interaction between the guide track 308 and the directional post 340. In particular, the post 340 cooperates with the receptor 310. When the guide 302 and the cutting device 304 are coupled, the drill head 336 is seated within the template 320.

After the guide 302 and the cutting device 304 are in proper position, the resected portion 14 is formed. With the drill head 336 activated, the cutting device 304 is maneuvered by the physician such that the post 340 traces the periphery of the guide track 308, thus causing the head 336 to cut resected portion 14, which has a shape that mirrors the shape of guide track 308. To insure that the head 336 cuts resected portion 14 having the proper size and shape, template 320 confines head 336 to the portion of the superior surface 12 where the resected portion 14 is desired. The dimensions of template 320 are slightly larger than the area of the desired resected portion 14 so that resected portion 14 can be formed without the head 336 contacting template 320.

The size and shape of resected portion 14 formed may be varied by outfitting the base 322 with a template insert 324 in which the guide track 308 and the template 320 have dimensions other than those illustrated in FIGS. 13, 15, and 16, these new dimensions closely approximate the desired dimensions and shape of resected portion 14.

As illustrated in FIG. 16, use of the fourth preparation device 300 to form resected portion 14 retains the entire rim 16 about the resected portion 14. Because the head 336 is supported above superior surface 12 by the cutting device 304, no portion of the rim 16 is removed during formation of the resected portion 14.

After the resected portion 14 is formed, the device 300 is removed from the tibia 10 and the implant 18 is seated and secured within the resected portion 14.

Before the resected portion 14 is formed, the superior articulating surface 12 is optionally prepared to provide a generally flat or planar surface upon which to cut the resected portion 14. Providing a planar superior surface 12 to be cut by a cutting device, such as device 20, 100, 200, or 300, provides a more precise cut of the resected portion 14.

Figure 17:
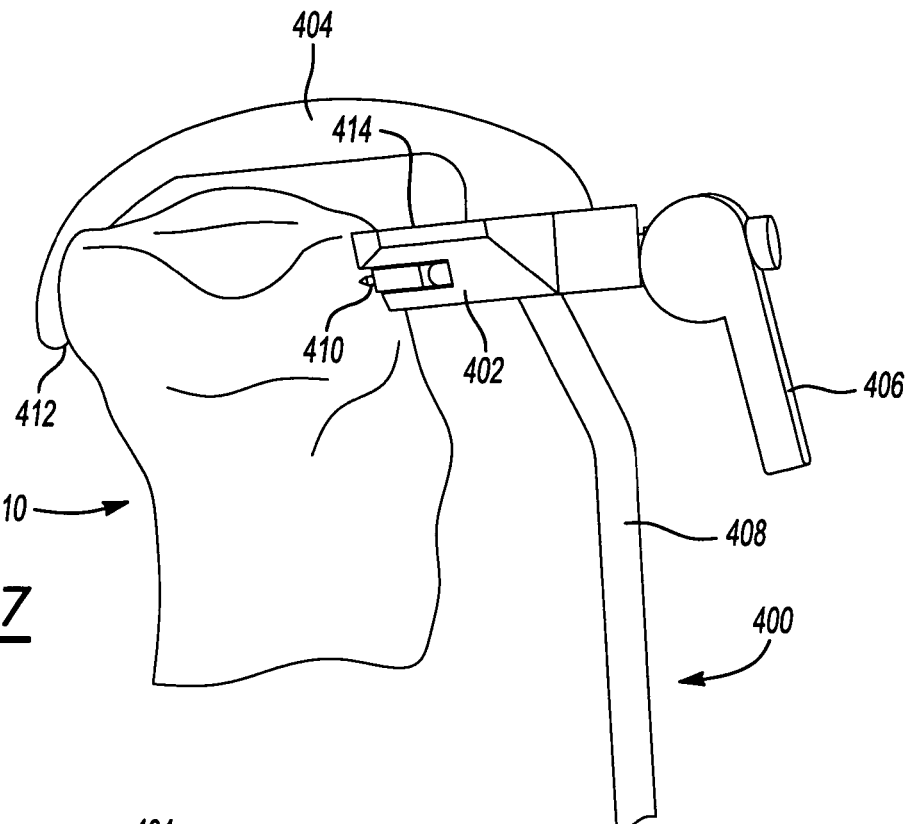
FIG. 17 is a side view of a surface guide used to level a bone surface before the surface is resected to receive an implant.

FIG. 17 illustrates a tibial surface guide 400 that may optionally be used to prepare the tibia 10 before cutting resected portion 14. While the surface guide 400 is illustrated and described in relation to the tibia bone 10, the surface guide 400 is operable for use with a variety of different bones in addition to the tibia 10.

The surface guide 400 generally includes a cutting base 402, a support rod 404, a fastening device 406, and an alignment rod 408. The cutting base 402 is a generally planar surface that provides a guide bar for a cutting device, such as a knife edge or a milling device. The base 402 includes at least one bone engaging device, such as pins 410.

The support rod 404 extends from the base 402 and is elevated above the base 402. At an end of the support rod 404 opposite the base 402 is positioned one or more bone engaging devices or pins 412. The pins 410 and the pins 412 are in substantially the same horizontal plane. The distance between the pins 410 and the pins 412 may be varied by actuation of fastening device 406. Typically, rotation of the fastening device 406 in a first direction will increase the distance between the pins 410 and 412, while rotation of the fastening device 406 in a second direction will decrease the distance between the pins 410 and 412. The position of the pins 410 relative to the pins 412 may be locked by locking the fastening device 406 into position.

The alignment rod 408 extends from the base 402 downward along the length of the tibia 10. The alignment rod 408 aids the physician in positioning the surface guide 400 and in leveling the superior articulating surface 12.

Figure 18:
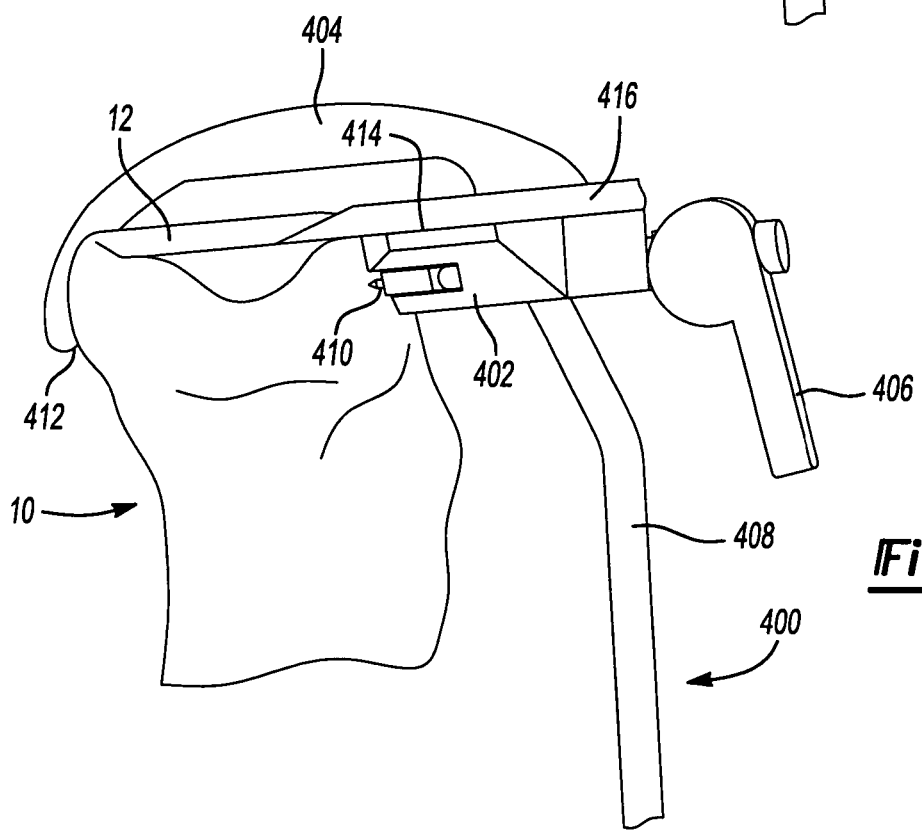
FIG. 18 is a side view of a bone being leveled using the surface guide of FIG. 17.

With reference to the FIG. 18, the operation of surface guide 400 will now be described. Surface guide 400 is first secured to the tibia 10 at or near the superior articulating surface 12. Specifically, the pins 410 and the pins 412 are positioned on opposite sides of tibia and the base 402 is positioned such that a cutting surface 414 of the base 402 is positioned at a point along the exterior of the tibia 10 that is equal to the desired depth of the leveling cut to be made. Also, using the alignment rod 408 as a reference, the guide 400 is set at the proper angle to effectuate a cut that is typically angled downward away from the eminence of the tibia. Once the base 402 is in proper position, the fastening device 406 is rotated to decrease the distance between the pins 410 and 412 so that the pins securely engage the tibia and hold the surface guide 400 into position. The pins 410 and 412 do not extend through the cortical surface of the bone 10 and thus do not weaken the bone or decrease the integrity of the bone structure.

Using the cutting surface 414 as a guide, a suitable cutting device, such as knife edge 416, is slid along surface to engage the articulating surface 12 of the tibia 10 and resect a small portion of the tibia 10 to create a generally planar portion in which to create resected portion 14. After the articulating surface 12 is leveled, the fastening device 406 is loosened to increase the distance between the pins 410 and the pins 412 such that the pins 410 and 412 no longer engage the tibia 10 and so that the surface guide can be removed.

In some instances it may also be necessary to treat a patient's femur in addition to, or instead of, the tibia 10. The preparation of a femur 500 to receive an implant, and the implantation of the implant, will now be described. However, it must be noted that the apparatuses and methods described below for treating the femur 500 may also be used to treat various other bones.

Figure 19:
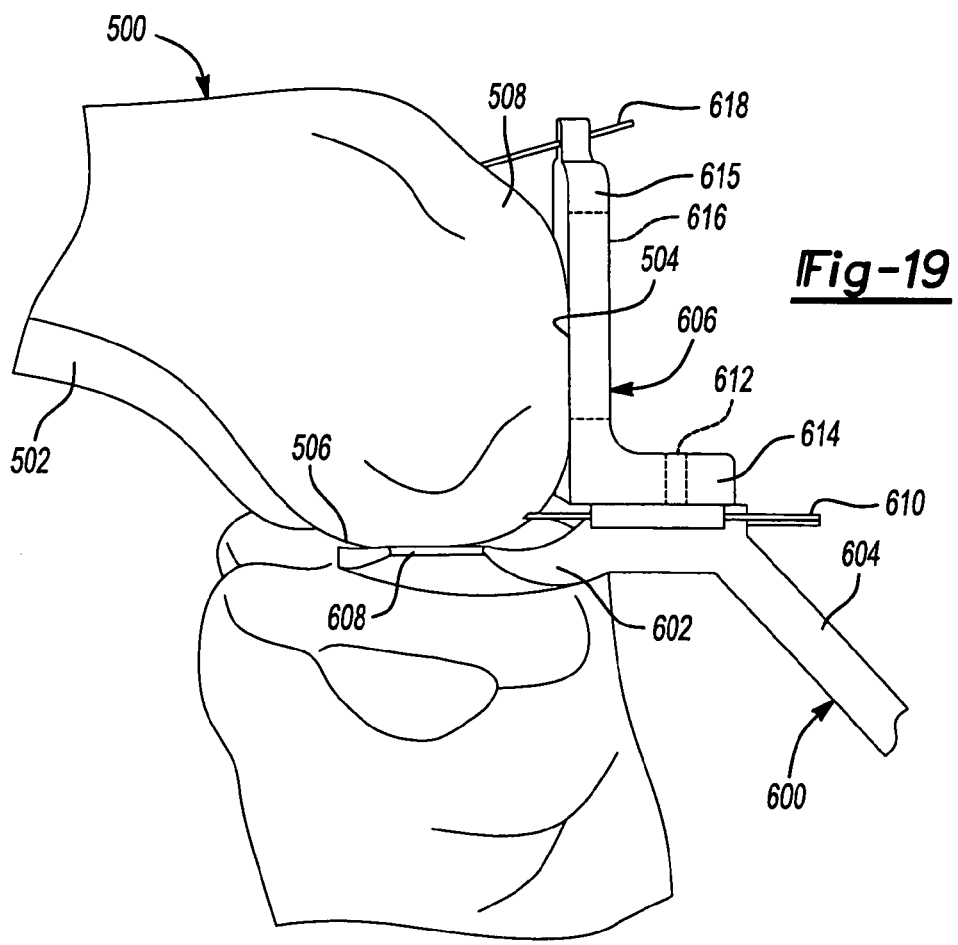
FIG. 19 is a side view of a cutting guide operable to prepare a bone for being resected to receive an implant.

With reference to FIG. 19, an inferior region of the femur 500 is illustrated. The inferior femur 500 generally includes a body 502, an inferior condyle surface 504, a posterior condyle surface 506, and an anterior condyle surface 508.

The inferior region of the femur 500 is prepared to receive an implant using a posterior condyle cutting guide 600. The cutting guide 600 generally includes a first resection guide 602 having a handle 604 and a second resection guide 606. The first resection guide 602 has a generally planar cutting surface 608 that is shaped to generally mirror the posterior condyle surface 506 of the femur 500. To secure the first resection guide 602 to the femur 500, the first resection guide 602 is equipped with a suitable fastening device, such as pins 610.

The second resection guide 606 is secured to the first resection guide 602 in any suitable manner, such as by a fastening pin 612. The second resection guide 606 typically includes a base portion 614 and an elongated guide portion 615. The elongated guide portion 615 includes an aperture or slit 616 for receiving a suitable cutting device. To help retain the second resection guide 606 into position, a suitable retention device, such as a pin 618, may be used to secure the guide 606 to the femur 500.

Use of the posterior condyle cutting guide 600 to prepare the femur 500 will now be described. Using the handle 604, the cutting guide 600 is inserted between the femur 500 and the tibia 10. The cutting guide 600 is positioned such that the planar cutting surface 608 closely abuts the posterior condyle surface 506 and so that the second resection guide 606 at least closely abuts the inferior condyle surface 504. After the cutting guide 600 is in proper position, the first resection guide 602 is secured to the femur 500 using pins 610 and the second resection guide 606 is pinned to the femur 500 using pins 618.

Figure 20:
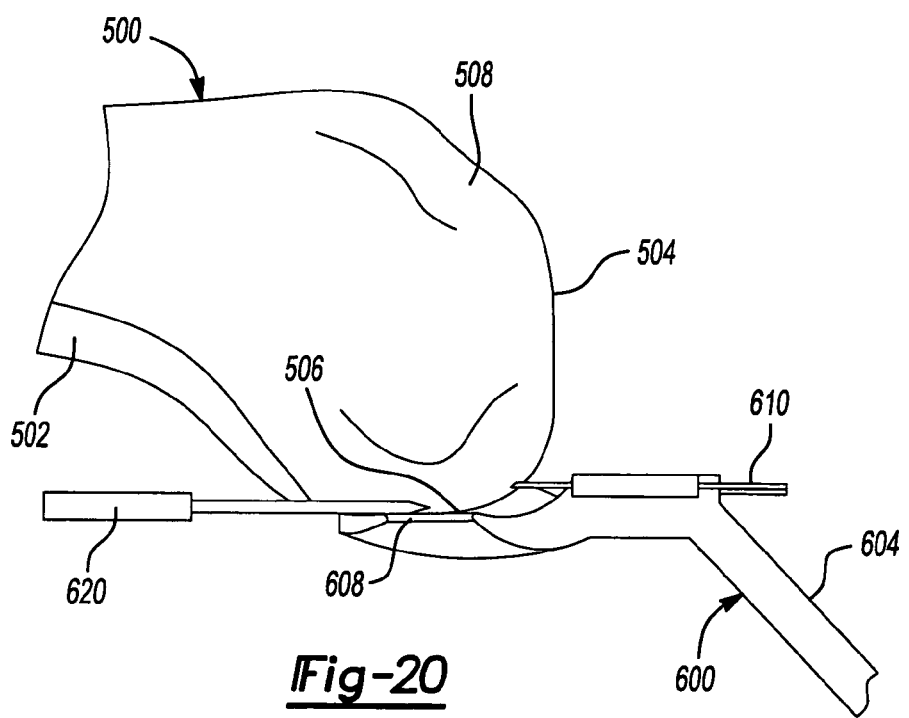
FIG. 20 is a side view illustrating the use of a first resection guide of the cutting guide of FIG. 19 to prepare a surface of a bone to receive an implant.

With the cutting guide 600 secured in position, a suitable cutting device, such as a pencil burr (not shown), is inserted through slit 616 to cut a recess in the inferior condyle surface 504. After the inferior condyle surface 504 is cut, the second resection guide 606 may be detached from first resection guide 602, leaving only the first resection guide 602 secured to the femur 500. As seen in FIG. 20, the planar cutting surface 608 is used as a guide for cutting the posterior condyle surface 506. For example, a push blade 620 maybe slid along the cutting surface 608 to cut the posterior condyle surface 506. After the posterior condyle surface 506 is cut, the first resection guide 602 is removed.

Figure 21:
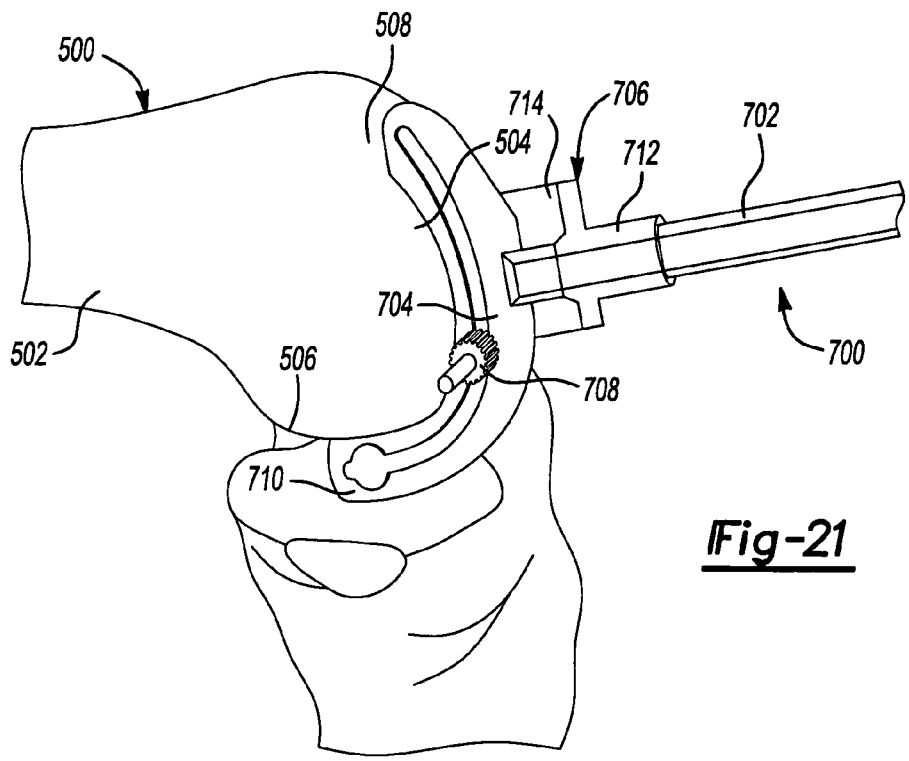
FIG. 21 is side view of a burr guide operable to prepare a bone surface to receive an implant.

In order for the femur 500 to receive a uni-condylar implant, portions of the inferior condyle surface 504, the posterior condyle surface 506, and the anterior condyle surface 508 must be removed to provide a suitable surface for the implant. To burr the posterior femur 500, a burr guide, such as burr guide 700, may be used. As illustrated in FIG. 21, burr guide 700 generally includes a positioning handle 702, a cutting device guide track 704, and an alignment device 706.

The positioning handle 702 is integrated with both the cutting device guide track 704 and the alignment device 706. Thus, manipulation of the handle 702 results in movement of both the guide track 704 and the alignment device 706. The positioning handle 702 typically takes the form of an elongated rod.

At one end of handle 702 is the guide track 704. The guide track 704 is generally curved to approximate the inferior condyle surface 504, the posterior condyle surface 506, and the anterior condyle surface 508. The guide track 704 receives a suitable cutting device, such as burr 708. The burr 708 is able to rotate within the guide track 704 as well as slide from one end of the guide track 704 to another end. The guide track 704 includes an aperture 710 at one end to permit introduction of the burr 708 to the guide track 704.

Also connected to handle 702 is the alignment device 706. The alignment device 706 includes a connection sleeve 712 and an alignment plate 714. The connection sleeve 712 connects the alignment device 706 to the handle 702. The alignment plate 714 extends from the connection sleeve 712 towards the guide track 704. The alignment plate 714 aids in positioning the guide 700 at the femur 500 by providing the physician with an alignment reference point.

With continuing reference to FIG. 21, the operation of burr guide 700 will now be described. Using handle 702, the operating physician directs the guide 700 to the femur 500 and positions the guide track 704 within a cut previously formed in the inferior femur 500, such as the cut made using the second resection guide 606. The alignment device 706 may also be used to help position the guide 700 at the femur 500.

Figure 22:
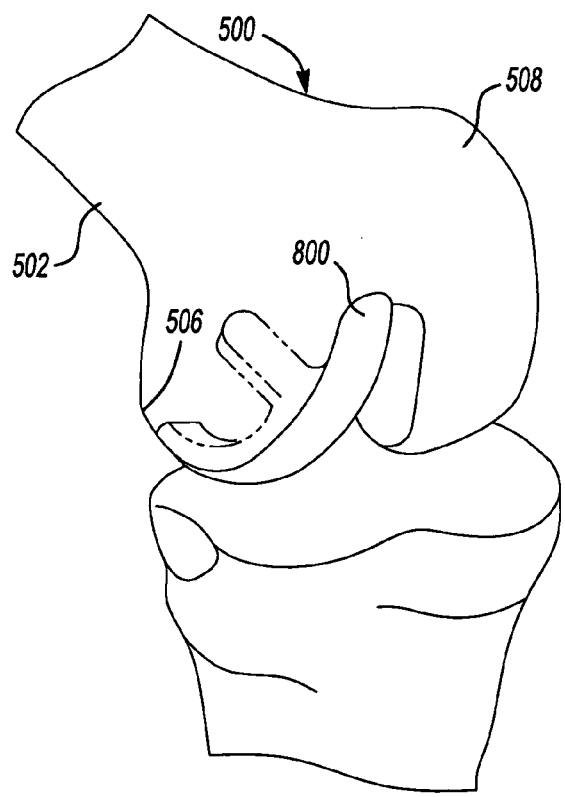
FIG. 22 is a side view of a bone prepared using the burr guide of FIG. 21, the bone having an implant seated within a recess formed by the burr guide of FIG. 21.

With the guide 700 in proper position, the burr 708 is inserted through the aperture 710 and seated in the guide track 704. The burr 708 is connected to a suitable power source, such as a drill (not shown), to effectuate rotation of the burr 708. The rotating burr 708 is brought into contact with the femur 500 to mill the femur 500 and create a recess to receive an implant 800 (FIG. 22). After the femur is cut, the guide 700 is removed and the implant 800 is placed within the recess and secured within the recess using a suitable adhesive, such as bone cement.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for preparing a bone to receive an implant comprising:
   an elongated resection guide operable to be secured to a bone, said elongated resection guide including:
      a first end;
      a second end opposite to said first end;
      a guide track at said first end, said guide track including a receptor that is movable within said guide track, said guide track is offset from a longitudinal axis of the bone when the resection guide is mounted to the bone; and
      a template at said second end, said template is co-planar with said guide track and has a shape defining an area of the bone to be resected, said template is positioned directly over the area of the bone to be resected and at least substantially surrounds the area when the resection guide is mounted to the bone; and
   a cutting device operable to cut the bone, said cutting device cooperates with said receptor in said guide track to restrict movement of said cutting device to a range of positions defined by said guide track and said template, said cutting device extends between said guide track and said template;
   wherein said elongated resection guide restricts movement of said cutting device to form a resected portion within the bone that is adapted to be at least substantially surrounded by a bone rim.

2. The system of claim 1, wherein the elongated resection guide is adapted to restrict movement of said cutting device to form the resected portion completely surrounded by the bone rim.

3. The system of claim 1, wherein said guide track and said template are provided in an insert that is selected from a variety of different inserts having guide tracks of different shapes and sizes based on the desired shape and size of said resected portion.

4. The system of claim 1, wherein said cutting device includes at least one guide cam operable to engage said receptor of said guide track.

5. The system of claim 1, wherein said cutting device comprises a side cutting mill.

6. The system of claim 1, wherein the bone is a tibia bone and engagement of the tibia by said cutting device is restricted to a superior surface of the tibia.

7. The system of claim 1, wherein said resection guide further comprises a first anchoring device operable to engage a first surface of the bone and a second anchoring device operable to engage a second surface of the bone, the distance between said first anchoring device and said second anchoring device being variable.

8. A system for preparing a bone to receive an implant comprising:
   a resection guide operable to be secured to the bone having a guide track and a template spaced apart from the guide track; and
   a side cutting mill operable to cut the bone and form a resected portion adapted to be at least substantially surrounded by a bone rim, said mill comprising at least one mating device operable to cooperate with said guide track;
   wherein cooperation between said guide track and said mating device restricts movement of said side cutting mill to the region of the resected portion, said mill extends between said guide track and said template along a longitudinal axis that is at least substantially perpendicular to a longitudinal axis of the bone when said resection guide is mounted to the bone; and
   wherein said template surrounds the resected portion when said resection guide is mounted to the bone to restrict movement of said mill beyond the resected portion and said guide track is spaced apart from a longitudinal axis of the bone.

9. The system of claim 8, wherein said resection guide is secured to both a superior region of the bone and an inferior region of the bone.

10. The system of claim 8, wherein said resection guide further comprises a removable insert having said guide track, said insert selected from a variety of different inserts having guide tracks of various different shapes and sizes based on the desired size and shape of the resected portion.

11. The system of claim 8, wherein said resection guide portion further comprises a first anchoring device operable to engage a first surface of the bone and a second anchoring device operable to engage a second surface of the bone, the distance between said first anchoring device and said second anchoring device being variable.

12. A system for preparing a bone to receive an implant comprising:
   a resection guide secured to the bone, said resection guide includes:
      a receptor with dimensions substantially similar to dimensions of a resected portion to be formed in the bone, said receptor is offset from a longitudinal axis of the bone when the resection guide is secured to the bone;
      a template that surrounds the resected portion; and
      a first anchoring device for engaging a first surface of the bone and a second anchoring device for engaging a second surface of the bone that is opposite to the first surface, a distance between the first anchoring device and the second anchoring device is variable to accommodate bones of different sizes; and
   a cutting device operable to cut the bone to form the resected portion, said cutting device extends through the template when said cutting device is mounted to said resection guide, said cutting device includes a directional device
   a positioning jig in cooperation with said receptor and operable to maneuver said cutting device;
   wherein cooperation between the directional device and the receptor prevents the cutting device from resecting the bone beyond the resected portion.

13. The system of claim 12, wherein said receptor comprises a recessed portion within said guide.

14. The system of claim 12, wherein said template includes dimensions substantially similar to dimensions of said receptor and said resected portion.

15. The system of claim 14, wherein said directional device and said cutting device are positioned at substantially similar positions within said receptor and said outline respectively to calibrate said device.

16. The system of claim 12, wherein said resection guide is chosen from a plurality of guides having different shapes and sizes based on the desired shape and size of the resected portion.

17. A resection guide for guiding a cutting device to a bone to prepare the bone to receive an implant, said resection guide comprising:
   a base;
   a template mounted to said base having a first end and a second end, said template including:
      a template outline at said first end having dimensions that define a predetermined area of the bone to be resected, the predetermined area adapted to be completely surrounded by a bone rim, the template outline positioned about the area of the bone to be resected when the resection guide is mounted to the bone;
      a guide track at said second end and in a common plane with the template outline that restricts movement of the cutting device to the predetermined area of the bone to be resected, the guide track is laterally offset from the template outline and the bone when the resection guide is mounted to the bone, the common plane is transverse to a longitudinal axis of the bone when the resection guide is mounted to the bone; and
      a support device that extends from the template to engage a cutting device;
   a first anchoring device operable to engage a first surface of the bone; and
   a second anchoring device operable to engage a second surface of the bone that is opposite to the first surface, the distance between said first anchoring device and said second anchoring device is variable by actuating a handle, the template outline positioned between the first anchoring device and the second anchoring device.

18. The resection guide of claim 17, wherein said template is removably mounted to said base.

19. The resection guide of claim 17, wherein said template is selected from a plurality of templates having template outlines of different dimensions.

20. The resection guide of claim 19, wherein said guide track includes a receptor that restricts movement of the cutting device.

21. An assembly for preparing a bone to receive an implant comprising:
- a side cutting mill for resecting the bone;
- a resection guide including:
  - a base; and
  - a template removably mounted to said base, said template including a template outline having dimensions that define a predetermined area of the bone to be resected, the predetermined area adapted to be completely surrounded by a bone rim and a guide track that receives a directional device of the cutting device to restrict movement of the cutting device to the predetermined area of the bone to be resected, said template and said guide track are in a common plane and spaced apart at opposite sides of the resection guide such that when said resection guide is mounted to the bone the template outline is mounted directly over the predetermined area of bone to be resected and the guide track is offset from a longitudinal axis of the bone, said template outline and said resection guide are permanently affixed in position along said template;
- a first anchoring device operable to engage a first surface of the bone; and
- a second anchoring device operable to engage a second surface of the bone that is opposite to the first surface, the distance between said first anchoring device and said second anchoring device is variable.

22. The assembly of claim 21, wherein said template is selected from a plurality of templates having template outlines of different sizes.

23. An assembly for preparing a bone to receive an implant comprising:
- a cutting device for resecting the bone including a guide feature and a directional device; and
- a resection guide including:
  - a base; and
  - a template removably mounted to said base, said template including a template outline at a first end of said template having dimensions that define a predetermined area of the bone to be resected, a support device that cooperates with said guide feature of said cutting device and a receptor movable within a guide track at a second end of said template that cooperates with said directional device of said cutting device, said template outline is positioned directly over the bone and the receptor is spaced apart from the bone along a longitudinal axis that is parallel with and spaced apart from a longitudinal axis of the bone when the resection guide is mounted to the bone, said guide track and said template outline are co-planar and positioned along a longitudinal axis of said template;
- wherein said predetermined area is adapted to be completely surrounded by a bone rim;
- wherein said receptor confines movement of said cutting device to prevent said cutting device from cutting outside said predetermined area; and
- wherein cooperation between said support device and said guide feature confines movement of said cuffing device to within a plane parallel to the longitudinal axis of said template.

24. The assembly of claim 23, wherein said template is selected from a plurality of templates having template outlines of different sizes.

25. The assembly of claim 23, wherein said guide feature comprises a recess.

26. The assembly of claim 23, wherein said directional device comprises a post.

27. The assembly of claim 23, wherein said support device comprises a post.

28. The assembly of claim 23, wherein said receptor comprises a recess.

* * * * *

UNITED STATES PATENT AND TRADEMARK OFFICE
CERTIFICATE OF CORRECTION

PATENT NO. : 7,608,079 B1  Page 1 of 1
APPLICATION NO. : 10/794709
DATED : October 27, 2009
INVENTOR(S) : Blackwell et al.

It is certified that error appears in the above-identified patent and that said Letters Patent is hereby corrected as shown below:

Column 2, Line 58
after "according", insert -- to --

Column 3, Line 4
after "is", insert -- a --

Column 3, Line 31
after "is", insert -- a --

Column 11, Line 46
"maybe" should be -- may be --

Column 16, Line 26, Claim 23
"cuffing" should be -- cutting --

Signed and Sealed this

Twenty-sixth Day of January, 2010

David J. Kappos
*Director of the United States Patent and Trademark Office*